United States Patent [19]
Aoi et al.

[11] Patent Number: 5,658,895
[45] Date of Patent: Aug. 19, 1997

[54] ANTICANCER ENTERAL FEEDING COMPOSITION

[75] Inventors: Shozo Aoi, Naruto; Goro Ebisu, Tokushima-ken, both of Japan

[73] Assignee: Otsuka Pharmaceutical Factory, Inc., Tokushima, Japan

[21] Appl. No.: 468,332

[22] Filed: Jun. 6, 1995

Related U.S. Application Data

[63] Continuation of Ser. No. 66,138, filed as PCT/JP92/01264, Sep. 30, 1992, abandoned.

[30] Foreign Application Priority Data

Oct. 7, 1991 [JP] Japan .................. 3-258883

[51] Int. Cl.$^6$ .................. A61K 31/715
[52] U.S. Cl. .................. 514/58; 514/400; 514/777; 514/778; 514/938; 426/602; 426/656; 426/658
[58] Field of Search .................. 514/58, 400, 777, 514/778, 938; 426/602, 656, 658

[56] References Cited

U.S. PATENT DOCUMENTS

| | | | |
|---|---|---|---|
| 4,670,268 | 6/1987 | Mahmoud | 426/72 |
| 5,278,149 | 1/1994 | Provost et al. | 514/23 |

FOREIGN PATENT DOCUMENTS

| | | |
|---|---|---|
| 0232652 | 8/1987 | European Pat. Off. |
| 0399341 | 11/1990 | European Pat. Off. |
| 2332027 | 6/1977 | France |
| 2029220 | 3/1980 | United Kingdom |

*Primary Examiner*—James H. Reamer
*Attorney, Agent, or Firm*—Sughrue, Mion, Zinn, Macpeak & Seas

[57] ABSTRACT

The invention provides an anticancer enteral feeding composition characterized by containing the described assortment of amino acids, fat and carbohydrate.

This anticancer enteral feeding composition can be smoothly administered orally or via a tube to achieve alimentation of cancer patients and inhibition of growth of tumor cells in the patients. Moreover, as used in combination with an anticancer chemotherapeutic agent, it synergistically potentiates the antitumor efficacy of the latter agent.

5 Claims, 6 Drawing Sheets

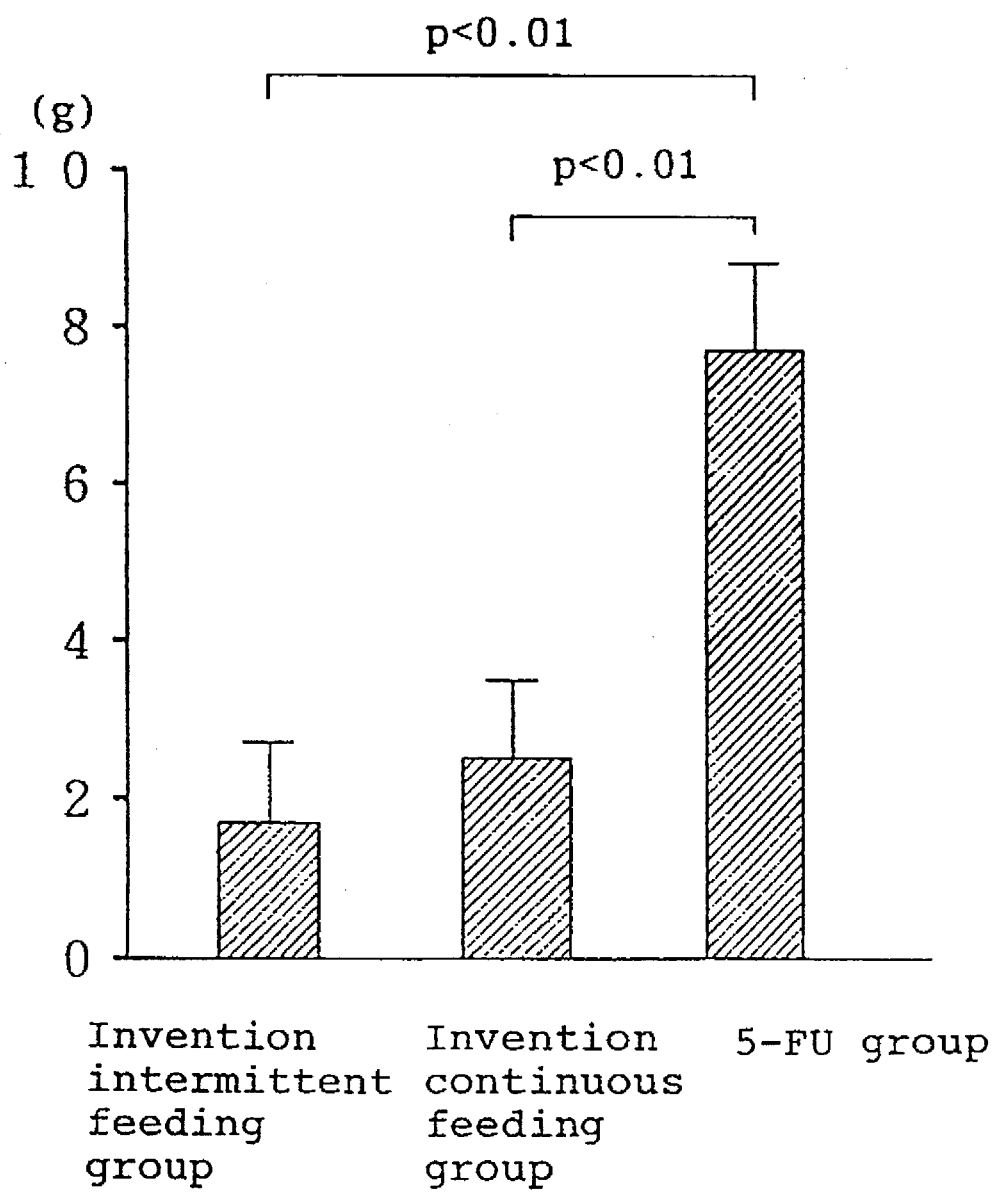

ANTICANCER ENTERAL FEEDING COMPOSITION

This is a Continuation of application Ser. No. 08/066,138 filed 27 May 1993, now abandoned, which is a 371 of PCT/JP92/01264, Sep. 30, 1992.

TECHNICAL FIELD

The present invention relates to a novel anti-cancer enteral feeding composition and more particularly to an anticancer enteral feeding composition designed according to the concept of amino acid imbalance and provided in dosage forms suitable for oral or tube feeding, which composition is effective in treating patients with cancer and improving malnutrition in such patients.

BACKGROUND ART

Multiple amino acid preparations, when given to a patient with cancer, assist in upholding physical strength due to their alimenting effect but, at the same time, nourish cancer cells as well to encourage growth and proliferation of the cancer cells so that the best which can be expected with such preparations is a delayed loss of body weight. In other words, it is a fatal disadvantage of those preparations that they do not alleviate clinical symptoms or contribute to body weight gain.

In an attempt to overcome these disadvantages, the inventors of the present invention had developed a new amino acid infusion not including any sulfur-containing amino acids such as methionine in accordance with the concept of amino acid imbalance (Japanese Kokai Patent Publication No. 35049/1980). However, since an amino acid preparation as a cancer therapy is generally administered in a total parenteral nutrition (TPN) regimen, there is a constant risk of hospital infection. Moreover, because as a rule the preparation is repeatedly administered for about 2 consecutive weeks, the patient must tolerate the inconveniences of an indwelling catheter for administration which restricts movement seriously over that long period. Furthermore, the total parenteral nutrition (TPN) must be given in several repetitions with about one-month-long intervals and that exerts a considerable mental burden on the patient. In addition, TPN generally entails marked atrophy of the digestive tract mucosa and, in that sense, parenteral administration is a negative factor in the functional homeostasis of the alimentary canal. Therefore, for patients with cancer, the development of an enteral feeding preparation compatible with oral and tube feeding has been awaited in earnest. Incidentally, from solubility and stability considerations, there are certain limits to the composition of a preparation of that type and in view of the necessity to correct nutritional deprivation in cancer patients, there is a true need for an enteral feeding formulation which may contain many other nutrients inclusive of carbohydrates, fats, vitamins and minerals as well.

The object of the present invention is to provide a novel enteral feeding composition which can be orally ingested, in lieu of said parenteral amino acid infusion, to nourish cancer patients and inhibit growth of cancer cells and which can be provided in a stable dosage form even when protein, fat and carbohydrate are additionally incorporated therein.

The intensive research done to accomplish the above object led the inventors to the finding that a powder obtainable by emulsifying a fat together with amino acids and spray-drying the emulsion gives, on addition of water, a stable oil-in-water emulsion without giving rise to insoluble matter, that when the above powder is mixed with granulated dextrin, there is obtained a feeding composition which can be very well dispersible in water, that the above composition is excellent in both nutritional competence and cancer cell growth inhibitory activity and that when used in conjunction with an anticancer drug, the composition synergistically potentiates its anticancer efficacy. The present invention has been conceived and developed on the basis of the above findings.

DISCLOSURE OF INVENTION

The invention is, therefore, directed to an anticancer enteral feeding composition characterized by comprising a powder obtainable by emulsifying a fat in an aqueous solution of protein source amino acids of the composition shown below in free amino acid equivalents and freeze-drying the resulting oil-in-water emulsion and in combination therewith granulated dextrin.

| L-Amino Acid | (g/100 g) |
| --- | --- |
| Isoleucine | 2.58–10.30 |
| Leucine | 4.21–16.82 |
| Lysine | 3.26–13.06 |
| Phenylalanine | 2.84–8.51 |
| Threonine | 1.89–5.67 |
| Tryptophan | 0.72–2.15 |
| Valine | 2.58–10.30 |
| Histidine | 1.46–4.38 |
| Arginine | 4.12–16.48 |
| Alanine | 2.15–8.58 |
| Aspartic acid and/or asparagine | 6.18–24.72 |
| Glutamic acid and/or glutamine | 10.31–41.22 |
| Glycine | 2.15–8.58 |
| Proline | 2.92–11.68 |
| Serine | 2.66–10.64 |
| Tyrosine | 0–3.0 |

Preferably, the anticancer enteral feeding composition of the present invention contains the following amino acids in the indicated proportions.

| L-Amino acid (g/100 g) | Preferred range | Optimal range |
| --- | --- | --- |
| Isoleucine | 2.58–7.73 | 3.86–6.44 |
| Leucine | 4.21–12.62 | 6.31–10.51 |
| Lysine | 3.26–9.80 | 4.90–8.16 |
| Phenylalanine | 2.84–8.51 | 4.25–7.09 |
| Threonine | 1.89–5.67 | 2.84–4.33 |
| Tryptophan | 0.72–2.15 | 1.07–1.79 |
| Valine | 2.58–7.73 | 3.86–6.44 |
| Histidine | 1.46–4.38 | 2.19–3.65 |
| Arginine | 4.12–12.36 | 6.18–10.30 |
| Alanine | 2.15–6.44 | 3.22–5.36 |
| Aspartic acid and/or asparagine | 6.18–18.54 | 9.27–15.45 |
| Glutamic acid and/or glutamine | 10.31–30.92 | 15.46–25.76 |
| Glycine | 2.15–6.44 | 3.22–5.36 |
| Proline | 2.92–8.76 | 4.38–7.30 |
| Serine | 2.66–7.98 | 3.99–6.65 |
| Tyrosine | 0–2.0 | 0–1.0 |

The above amino acid formula has been selected with the following fact taken into consideration. Thus, anticancer drugs in general are known to impair the alimentary tract mucosa of cancer patients (Journal of Parenteral and Enteral Nutrition, Vol. 14, No. 4, Supplement 100S–105S, for instance). Therefore, any enteral feeding formula for cancer therapy preferably contains glutamine, an amino acid having gastrointestinal mucosal protecting activity, in an appropriate proportion. The above formula takes that fact into consideration.

The present invention further provides an anti-cancer enteral feeding composition containing, in each 2000 kcal equivalent of the total composition, 40 to 100 g of amino acids, 11.1 to 66.6 g of fat and 250 to 435 g of dextrin and an anticancer enteral feeding composition prepared using an emulsifier with an HLB number of 9 to 16 in a proportion of 2.5 to 10% by weight relative to the total weight of fat and amino acids.

The composition of the present invention is not only capable of inhibiting growth of cancer cells and correcting the malnutrition of cancer patients but is stable without exerting an undue burden on the patient even in long-term therapy and, when supplied in powdery form, is so highly soluble in water that it can be neatly dissolved by mere addition of water in the hospital without using a mixer or the like which is conventionally required for homogenization. Having those advantageous characteristics, the anticancer enteral feeding composition of the instant invention can be provided in a pharmaceutical or dosage form compatible with oral or tube feeding for cancer patients, thus being sharply distinguished from any prior art preparation.

The composition of the present invention essentially contains an assortment of the above-mentioned amino acids in the indicated proportions as a protein source. That amino acid composition as a protein source is in common with the composition of the previous invention disclosed in the Japanese application filed in the name of the present applicant in respect of the absence of sulfur-containing amino acids such as methionine and is especially beneficial from the standpoint of inhibiting growth of tumor cells.

The respective amino acids constituting said protein source are L-forms and preferably crystalline L-amino acids. Although those amino acids are generally used in the free form, that is not an absolute requirement. Thus, for example, the amino acids can be used in the form of pharmaceutically acceptable salts such as salts with alkali metals, e.g. sodium salts, potassium salts, etc., salts with mineral acids, e.g. hydrochlorides, sulfates, etc., or salts with organic acids, e.g. acetates, lactates, malates, etc. or even in the form of esters which are hydrolyzed to the corresponding free amino acids in the recipient body. Among specific examples of such salts and esters are L-lysine hydrochloride, L-lysine acetate, L-lysine malate, L-arginine hydrochloride, L-histidine hydrochloride monohydrate, L-phenylalanine methyl ester, L-phenylalanine ethyl ester and so on. Furthermore, the above amino acids may be used, either as a whole or partially, in the form of N-acyl derivatives such as N-acetyl-L-tryptophan. The utilization of an amino acid in the form of such a derivative is particularly effective when the amino acid as it is sparingly soluble and may undergo precipitation. Furthermore, the above-mentioned amino acids can be used in the form of oligopeptides which are formed as two or more amino acids of the same kind or different kinds are linked to each other by way of peptide linkage. As specific examples of such oligopeptides, there may be mentioned L-arginyl-L-leucine, L-threonyl-L-phenylalanine, L-leucyl-L-lysine, L-alanyl-L-glutamine, L-glycyl-L-glutamine and so on. When the amino acids are used in any of the above-mentioned various forms other than the free form, the free amino acid equivalents should fall with the respective ranges specified hereinbefore.

In the manufacture of an anticancer enteral feeding composition of the present invention for oral feeding, the incorporation of non-essential amino acids such as alanine, glycine, aspartic acid, asparagine, glutamic acid, glutamine, proline and serine is favorable to the taste of the composition and, therefore, desirable.

In providing an anticancer enteral feeding composition of the present invention, it is an essential requisite to employ a powder obtainable by emulsifying a fat in an aqueous solution of the above specified protein source amino acids and spray-drying the resulting oil-in-water emulsion.

The fat mentioned above may be any and all of the substances well known as energy sources and as specific examples of fat, there may be reckoned vegetable fats and oils such as soybean oil, corn oil, palm oil, etc. and animal fats and oils such as beef tallow, lard, fish oil and so on. Those substances can be used alone or in combination.

Another indispensable feature of the present invention resides in the use of granulated dextrin (hereinafter sometimes referred to as carbohydrate) in combination with the above-mentioned powder.

The proportions of said protein source, fat and carbohydrate in the composition of the present invention are preferably within the following ranges, assuming that the caloric value of amino acids is 4 kcal/g, that of fat is 9 kcal/g and that of dextrin is 4 kcal/g. Thus, on the basis of each 2000 kcal of the total preparation, the protein source should account for 40 to 100 g, fat for 11.1 to 66.7 g and carbohydrate for 250 to 435 g, or more preferably, the protein source should account for 50 to 80 g, fat for 11.1 to 44.4 g and carbohydrate for 320 to 425 g. The incorporation of fat in the above range not only makes up for any deficiency in essential fatty acids in the composition but insures a rounded-off taste in an oral dosage form as well as improved nutritional competence. On the other hand, the incorporation of carbohydrate in the above range not only imparts sweetness to the composition but improves its nutritional potential.

The composition of the present invention may contain minerals, vitamins, stabilizers, biocides, preservatives and other common auxiliary agents in addition to said essential protein source, fat and carbohydrate. Among said minerals are inorganic or organic electrolyte salts capable of supplying sodium, potassium, magnesium, phosphorus, iron, copper, manganese, zinc, etc., such as sodium chloride, potassium chloride, magnesium sulfate, manganese sulfate, zinc sulfate, iron sulfate, copper sulfate, calcium glycerophosphate, iron sodium succinato-citrate and so on. Among said vitamins are vitamin A, vitamin $B_1$, vitamin $B_2$, vitamin $B_6$, nicotinamide, pantothenic acid, vitamin $B_{12}$, vitamin C, vitamin D, vitamin E, biotin, phytonadione, folic acid, calcium pantothenate, choline bitartarate and so on. Said stabilizers may for example be natural polysaccharides such as guar gum, pectin, locust bean gum, xanthane gum, tragacanth gum, carrageenin, and so on. Among said preservatives are benzoic acid, sorbic acid, propionic acid, dehydroacetic acid, inclusive of their salts, salicylic acid, p-hydroxybenzoic esters and so on. As a pH control agent, citric acid, for instance, can be incorporated. The levels of addition of said vitamins and minerals may not be different from those commonly employed in the art and are preferably sufficient in threpsological terms. In the composition of the invention for oral ingestion, a flavor and the like can be incorporated for further improving the palatability of the composition.

The composition of the invention can be manufactured in the following manner. Thus, specified amounts of protein source amino acids are first dissolved well in an appropriate quantity of water. Generally, the concentration of the amino acids in the solution is preferably in the range of about 10 to 20% (w/v). To that aqueous solution may be added, where necessary, various components other than said carbohydrate, namely vitamins, minerals and so on. Then, a sufficient amount of fat to give the specified final proportion, as well as an emulsifier, is added to the aqueous solution and the mixture is emulsified in the per se conventional manner to prepare an oil-in-water emulsion. The emulsifier to be used for that purpose may typically be soya lecithin, a sucrose fatty acid ester (HLB ca. 9–16) or the like. The amount of such emulsifier is preferably selected within the range of about 2.5 to 10 weight % based on the total weight of the fat and amino acids. The temperature of the emulsification system is not so critical but may generally be in the range of about 60° to 80° C. The emulsion thus prepared is spray-dried to give a powder composed of the fat and amino acids. Finally the specified amount of said carbohydrate is mixed with the above powder followed, where necessary, by addition of other additional components such as vitamins and minerals. The resulting mixture is accommodated in a suitable container, such as an aluminum-laminated film bag or the like, preferably with nitrogen gas purging. In the above manner, the desired composition of the present invention can be manufactured.

The anticancer enteral feeding composition manufactured in the above manner is generally diluted with water so that the pH of the dilution will be about 5.5 to 7.0, preferably about 6.0 to 6.5, and administered in the liquid form orally or by tube feeding. As an alternative, the powdery preparation, either as it is or as formulated with an appropriate excipient, can be supplied for ingestion in the solid form. In either mode of use, the desired nourishing and anticancer effects can be expected.

While the composition of the present invention can provide an anticancer effect of its own, the anticancer effect of the composition can be potentiated by using it in conjunction with various anticancer drugs which are commonly known as cancer chemotherapeutic agents. The other way around, the enteral feeding composition of the present invention potentiates the anticancer effect of said anticancer drugs. Therefore, the present invention further provides an enteral feeding composition for use in combination with such anticancer drugs and a multiple drug therapy involving both of them.

The anticancer drugs which can be used concomitantly with the composition of the invention include various known drugs, e.g. fluorinated pyrimidine anticancer agents such as 5-fluorouracil (5-FU, Kyowa Hakko Kogyo), Futraful (Taiho Pharmaceutical), BOF-A2 (Otsuka Pharmaceutical), UFT (Taiho Pharmaceutical), Furtulon (Nippon Roche) etc., cisplastin (tradename: Randa Inj., Nippon Kayaku), Oncovin (Shionogi & Co.), mitomycin (Kyowa Hakko Kogo) and so on. Particularly preferred is a combination therapy with a fluorinated pyrimidine anticancer agent. Thus, as shown in Test Example 4 hereinafter, the anticancer enteral feeding composition of the present invention has a mechanism of action producing a marked depression of methionine level in the cancer cell, with an associated effect on folic acid metabolism within the cancer cell to increase the intracellular level of 5,10-methylenetetrahydrofolate and induce formation of a ternary complex with FdUMP, which is the active form of 5-FU, and thymidylate synthetase (TS) with an increased incidence to inhibit TS activity and synergistically potentiate the antitumoral activity of 5-FU. Furthermore, as will be seen from Test Examples 2, 3, 5 and 6 hereinafter, the combined use of the anticancer enteral feeding composition of the invention and 5-FU produces a synergististic anticancer or antitumor effect. Incidentally, Test Examples 2 and 3 show the results obtained when the enteral feeding composition of the invention was continuously administered by tube feeding, Test Example 5 shows the results obtained when the same composition was given for ingestion ad libitum, and Test Example 6 shows the results obtained when the composition was administered through the tube intermittently.

In performing a multiple drug therapy using any of the various anticancer drugs mentioned above, such anticancer drug or drugs may be mixed with the composition of the invention beforehand and the mixture be administered in one unit dosage form and the present invention provides such multi-drug preparations as well. The manufacture of such multi-drug preparations can be performed in the same manner as described hereinbefore except that pharmacologically effective amounts of such concomitant anticancer agents are incorporated.

The above-mentioned multi-drug combination therapy covers cases in which said anticancer drugs are orally or intravenously administered independently of the administration of the anticancer enteral feeding composition of the invention. In such cases, too, the dosage or amount of each concomitant anticancer agent is the usual pharmacologically effective amount of the particular agent and can be selected according to each species of anticancer drug.

The anticancer enteral feeding composition of the invention is prepared in forms suitable for oral administration or tube feeding and the ingestion or administration of such a preparation produces both nourishing and anticancer effects. The amount of ingestion or dosage level can be selected with reference to the specific dosage form, the patient's clinical condition, the therapeutic effect desired, etc. and, therefore, cannot be stated in general terms. Roughly speaking, however, an amount (protein 50 to 70 g) corresponding to about 1500 to 2000 kcal/day may be administered to each adult patient. The concentration for tube feeding is preferably about 0.5 to 2.0 kcal/ml. For oral feeding, however, there is virtually no limitation and the composition can be ingested in the form of a concentrated solution or as previously processed into a concentrated jelly or the like.

BRIEF DESCRIPTION OF THE DRAWINGS

FIG. 6 is a diagrammatic representation of the tumor growth inhibitory effect of the combined use of the composition of the invention and an anticancer drug in Test Example 6.

BEST MODE FOR CARRYING OUT THE INVENTION

Figure 1:
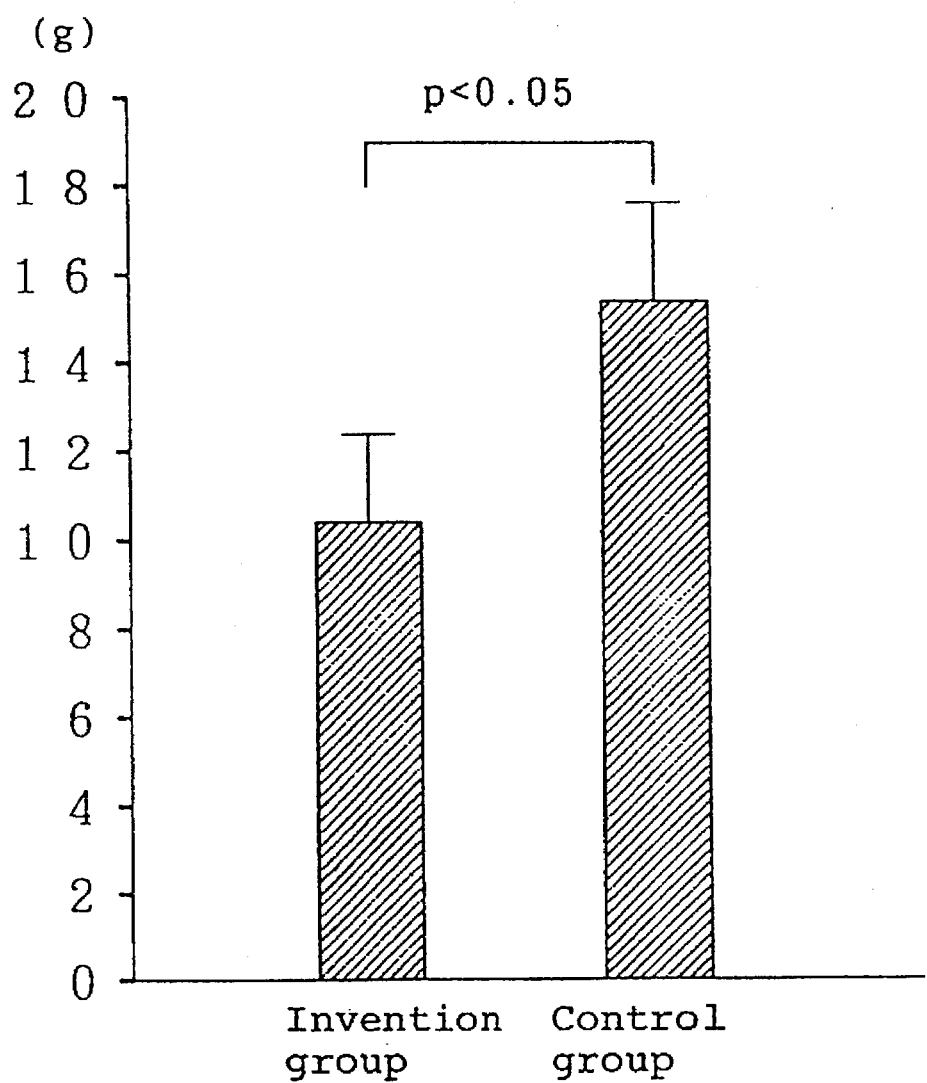
FIG. 1 is a diagrammatic representation of the tumor growth inhibitory effect of the composition of the invention as determined in Test Example 1.

The following are preparation examples of the anticancer enteral feeding composition of the invention and test examples using the enteral feeding compositions of the invention.

Example 1

In 5000 ml of purified water were dissolved the following amino acids in the respective amounts indicated in Table 1, with heating at about 70° to 80° C.

TABLE 1

| Amino acid formula (g) | |
|---|---|
| L-Isoleucine | 36 |
| L-Arginine | 58 |
| L-Leucine | 59 |
| L-Alanine | 30 |
| L-Lysine acetate | 65 |
| L-Aspartate (Na) | 113 |
| L-Phenylalanine | 40 |
| L-Glutamine | 144 |
| L-Threonine | 27 |
| Glycine | 30 |
| L-Tryptophan | 10 |
| L-Proline | 41 |
| L-Valine | 36 |
| L-Serine | 37 |
| L-Histidine HCl | 28 |
| (Total amino acid: | 754) |

On the other hand, 10 g of soya lecithin (Epikuron 100, Nihon Sieber Hegner) were dissolved in 222 g of soybean oil (Nippon Oils and Fats) with heating, while 30 g of sucrose fatty acid ester (DK-F160, Daiichi Kogyo Seiyaku, HLB=15) were dissolved in 1000 ml of purified water with heating.

The three solutions prepared as above were blended and emulsified in a homogenizer (Manton-Gauin; Doei Shoji). The resulting emulsion was dried using a spray-dryer (ADV-Anhydro) to give 910 g (100%=1016 g) of a mixed fat-amino acid powder.

Then, 510 g of the above mixed powder, 1800 g of granulated dextrin (Matsutani Chemical) and a mixture of the minerals and vitamins indicated below in Tables 2 and 3 in 100 g of the same dextrin were uniformly blended and the resulting mixture was filled into 25 aluminum-laminated film bags with nitrogen gas purging and sealing to provide an enteral feeding composition of the invention (400 kcal/100 g bag).

TABLE 2

| [Mineral formula] (g) | |
|---|---|
| Potassium chloride | 18 |
| Zinc sulfate | 0.3 |
| Calcium glycerophosphate | 26.22 |
| Iron sulfate | 0.3 |
| Magnesium sulfate | 15 |
| Copper sulfate | 0.04 |
| Manganese sulfate | 0.055 |
| Potassium sorbate | 2.5 |

TABLE 3

| [Vitamin formula] | |
|---|---|
| Retinol paimitate | 20000 IU |
| Tocopherol acetate | 200 mg |
| Bisbentiamine | 22 mg |
| Phytonadione | 10 mg |
| Riboflavine | 18 mg |
| Nicotinamide | 200 mg |
| Pyridoxine HCl | 24.5 mg |

TABLE 3-continued

| [Vitamin formula] | |
|---|---|
| Folic acid | 2 mg |
| Cyanocobalamine | 0.025 mg |
| Calcium pantothenate | 82 mg |
| Sodium ascorbate | 1125 mg |
| Biotin | 0.3 mg |
| Cholecalciferol | 2000 IU |
| Choline bitartarate | 835 mg |

EXAMPLES 2–17

The anticancer enteral feeding compositions shown below in Table 4 were manufactured in the same manner as Example 1. It should be noted that as the fat and carbohydrate, the same soybean oil (Nippon Oils and Fats) and dextrin (Matsutani Chemical) as used in Example 1 were employed.

TABLE 4

| Amino acid (g/100 g total amino acid) | Ex. 2 | Ex. 3 | Ex. 4 | Ex. 5 |
|---|---|---|---|---|
| L-Isoleucine | 6.0 | 5.2 | 6.4 | 3.7 |
| L-Leucine | 9.5 | 7.3 | 10.3 | 9.7 |
| L-Lysine (L-lysine acetate) | 7.3 | 5.7 | 4.7 | 10.0 |
| L-Phenylalanine | 6.5 | 6.8 | 7.4 | 4.5 |
| L-Threonine | 4.8 | 4.2 | 2.8 | 2.6 |
| L-Tryptophan | 1.7 | 1.2 | 0.8 | 0.8 |
| L-Valine | 7.8 | 5.7 | 5.1 | 7.3 |
| L-Histidine (L-hystidine HCl) | 2.7 | 3.0 | 1.5 | 3.9 |
| L-Arginine | 6.3 | 7.5 | 8.6 | 6.8 |
| L-Alanine | 6.7 | 7.3 | 3.7 | 5.0 |
| L-Aspartic acid (Sodium L-aspartate) | 4.6 | 11.0 | 14.1 | 3.5 |
| L-Asparagine | 6.8 | 0 | 0 | 6.0 |
| L-Glutamic acid (Sodium L-glutamate $H_2O$) | 0 | 7.0 | 0 | 10.9 |
| L-Glutamine | 14.5 | 8.6 | 20.0 | 10.7 |
| Glycine | 3.9 | 4.1 | 2.9 | 2.8 |
| L-Proline | 3.9 | 5.1 | 4.3 | 7.6 |
| L-Serine | 7.0 | 9.4 | 6.8 | 4.2 |
| L-Tyrosine | 0 | 0.9 | 0.6 | 0 |
| In 2000 kcal of the preparation: | | | | |
| Total amino acid (g) | 70 | 80 | 65 | 40 |
| Fat (g) | 22.2 | 11.1 | 44.4 | 55.6 |
| Dextrin (g) | 380 | 395 | 335.1 | 334.9 |

| Amino acid (g/100 g total amino acid) | Ex. 6 | Ex. 7 | Ex. 8 | Ex. 9 |
|---|---|---|---|---|
| L-Isoleucine | 3.7 | 8.0 | 7.0 | 4.2 |
| L-Leucine | 4.5 | 4.8 | 4.8 | 4.5 |
| L-Lysine (L-lysine acetate) | 6.7 | 9.6 | 6.3 | 4.3 |
| L-Phenylalanine | 3.0 | 3.3 | 3.3 | 3.2 |
| L-Threonine | 1.9 | 2.0 | 2.0 | 2.0 |
| L-Tryptophan | 0.8 | 1.7 | 1.7 | 1.8 |
| L-Valine | 2.6 | 3.0 | 3.0 | 2.9 |
| L-Histidine (L-hystidine HCl) | 1.7 | 1.5 | 1.5 | 1.7 |
| L-Arginine | 6.5 | 5.0 | 5.0 | 4.5 |
| L-Alanine | 2.5 | 2.3 | 2.2 | 6.2 |
| L-Aspartic acid (Sodium L-aspartate) | 12.8 | 11.1 | 10.2 | 10.0 |
| L-Asparagine | 11.8 | 0 | 0 | 0 |
| L-Glutamic acid (Sodium L-glutamate $H_2O$) | 15.7 | 30.0 | 39.0 | 10.0 |

TABLE 4-continued

| | | | | |
|---|---|---|---|---|
| L-Glutamine | 17.2 | 0 | 0 | 30.9 |
| Glycine | 2.3 | 5.4 | 4.4 | 4.5 |
| L-Proline | 3.1 | 9.6 | 6.6 | 6.3 |
| L-Serine | 2.7 | 2.7 | 3.0 | 2.8 |
| L-Tyrosine | 0.5 | 0 | 0 | 0.2 |

In 2000 kcal of the preparation:

| | | | | | |
|---|---|---|---|---|---|
| Total amino acid | (g) | 80 | 60 | 65 | 80 |
| Fat | (g) | 60.5 | 40.3 | 52.1 | 24.6 |
| Dextrin | (g) | 283.8 | 349.3 | 317.7 | 364.6 |

| Amino acid (g/100 g total amino acid) | Ex. 10 | Ex. 11 | Ex. 12 | Ex. 13 |
|---|---|---|---|---|
| L-Isoleucine | 9.9 | 8.9 | 7.9 | 6.1 |
| L-Leucine | 5.2 | 4.3 | 4.3 | 15.0 |
| L-Lysine (L-lysine acetate) | 4.3 | 3.4 | 3.4 | 3.4 |
| L-Phenylalanine | 3.1 | 4.0 | 2.9 | 2.9 |
| L-Threonine | 2.0 | 2.1 | 2.0 | 2.0 |
| L-Tryptophan | 1.5 | 0.8 | 0.8 | 0.8 |
| L-Valine | 2.8 | 2.6 | 5.3 | 2.6 |
| L-Histidine (L-hystidine HCl) | 1.6 | 1.6 | 1.6 | 1.6 |
| L-Arginine | 4.6 | 4.3 | 10.0 | 7.9 |
| L-Alanine | 4.0 | 5.4 | 3.4 | 4.7 |
| Aspartic acid (Sodium L-aspartate) | 20.6 | 15.9 | 10.9 | 10.1 |
| L-Asparagine | 0 | 8.0 | 5.2 | 0 |
| L-Glutamic acid (Sodium L-glutamate H$_2$O) | 10.0 | 8.0 | 10.2 | 0 |
| L-Glutamine | 18.2 | 13.2 | 4.2 | 23.0 |
| Glycine | 4.6 | 4.9 | 8.4 | 4.6 |
| L-Proline | 3.0 | 5.8 | 9.0 | 8.5 |
| L-Serine | 4.5 | 6.4 | 10.5 | 6.8 |
| L-Tyrosine | 0.1 | 0.4 | 0 | 0 |

In 2000 kcal of the preparation:

| | | | | | |
|---|---|---|---|---|---|
| Total amino acid | (g) | 80 | 70 | 75 | 75 |
| Fat | (g) | 32.5 | 48.1 | 38.0 | 27.0 |
| Dextrin | (g) | 346.8 | 321.7 | 339.5 | 364.2 |

| Amino acid (g/100 g total amino acid) | Ex. 14 | Ex. 15 | Ex. 16 | Ex. 17 |
|---|---|---|---|---|
| L-Isoleucine | 5.4 | 9.3 | 9.3 | 6.3 |
| L-Leucine | 13.0 | 11.0 | 9.0 | 8.0 |
| L-Lysine (L-lysine acetate) | 13.0 | 3.8 | 3.4 | 3.4 |
| L-Phenylalanine | 2.9 | 3.0 | 2.9 | 2.9 |
| L-Threonine | 2.0 | 2.0 | 2.0 | 2.0 |
| L-Tryptophan | 0.8 | 1.8 | 0.8 | 0.8 |
| L-Valine | 2.6 | 9.6 | 2.6 | 5.8 |
| L-Histidine (L-hystidine HCl) | 1.6 | 1.6 | 1.6 | 1.6 |
| L-Arginine | 4.2 | 4.3 | 16.3 | 12.3 |
| L-Alanine | 3.5 | 4.6 | 8.3 | 7.8 |
| L-Aspartic aicid (Sodium L-aspartate) | 7.0 | 6.5 | 7.9 | 12.1 |
| L-Asparagine | 3.0 | 0 | 0 | 1.5 |
| L-Glutamic acid (Sodium L-glutamate H$_2$O) | 0 | 4.8 | 0 | 9.1 |
| L-Glutamine | 30.0 | 17.0 | 17.1 | 12.1 |
| Glycine | 2.3 | 7.1 | 5.2 | 5.2 |
| L-proline | 5.1 | 10.0 | 9.0 | 3.0 |
| L-Serine | 3.6 | 3.6 | 4.6 | 6.1 |
| L-Tyrosine | 0 | 0 | 0 | 0 |

In 2000 kcal of the preparation:

| | | | | | |
|---|---|---|---|---|---|
| Total amino acid | (g) | 80 | 60 | 80 | 80 |
| Fat | (g) | 60.0 | 14.6 | 20.0 | 46.5 |
| Dextrin | (g) | 285 | 407.1 | 375 | 315.3 |

EXAMPLES 18–21

The amino acids shown in Table 5 in the indicated amounts were dissolved in water to provide aqueous solutions each with a total amino acid content of 70 g/2000 ml (Enteral feeding compositions of the invention).

EXAMPLE 22

A total of 70 g of the same amino acids in the same respective amounts as used in Example 18 was dissolved in 1000 ml of water with heating at about 70°–80° C. On the other hand, 3 g of sucrose fatty acid ester (DK-160, Daiichi Kogyo Seiyaku) were similarly dissolved in 100 ml of water with heating, while 1 g of soya lecithin (Epikuron 100, Nihon Sieber Hegner) was dissolved in 22.2 g of soybean oil (Nippon Oils and Fats) with heating to prepare a fat component. The above three solutions were combined and emulsified in an emulsifier (Manton-Gaulin, Doei Shoji). To the emulsion was added a sufficient amount of water to make 2000 ml. In that manner, an emulsion (an enteral feeding composition of the invention) was obtained. The composition of that preparation is shown in Table 5.

EXAMPLE 23

A total of 70 g of the same amino acids in the same respective amounts as those used in Example 18 and, as a carbohydrate, 380 g of dextrin (Matsutani Chemical) were dissolved in sufficient water to make 2000 ml. The composition of that aqueous solution (an anticancer enteral feeding composition of the invention) is shown in Table 5.

EXAMPLE 24

To an emulsion prepared in the same manner as Example 22 were added 380 g of dextrin (Matsutani Chemical) and a sufficient amount of water to make 2000 ml. The procedure gave an emulsion (an anticancer enteral feeding composition of the invention), the composition of which is shown in Table 5.

Comparative Example 1

In the same manner as Example 18, a control aqueous solution of the amino acid composition indicated in Table 5 was manufactured.

Comparative Example 2

In the same manner as Example 22, a control emulsion of the composition indicated in Table 5 was manufactured.

Comparative Example 3

In the same manner as Example 23, a control aqueous solution of the composition indicated in Table 5 was manufactured.

Comparative Example 4

In the same manner as Example 24, a control emulsion of the composition indicated in Table 5 was manufactured.

TABLE 5

| Amino acid (g/100 g) | Example No. | | | | |
|---|---|---|---|---|---|
| | 18 | 19 | 20 | 21 | 22 |
| L-Isoleucine | 5.2 | 6.0 | 5.2 | 3.7 | 5.2 |
| L-Leucine | 8.4 | 9.5 | 7.3 | 9.7 | 8.4 |
| L-Lysine | 6.5 | 10.4 | 8.1 | 14.1 | 6.5 |

TABLE 5-continued

| | | | | | |
|---|---|---|---|---|---|
| L-Phenylalanine | 5.7 | 6.5 | 7.0 | 4.5 | 5.7 |
| L-Threonine | 3.8 | 4.8 | 4.2 | 2.6 | 3.8 |
| L-Tryptophan | 1.4 | 1.7 | 1.2 | 0.8 | 1.4 |
| L-Tyrosine | 0 | 0 | 0.9 | 3.0 | 0 |
| L-Valine | 5.2 | 7.8 | 5.7 | 7.3 | 5.2 |
| L-Histidine | 2.9 | 3.6 | 4.1 | 5.3 | 2.9 |
| L-Arginine | 8.2 | 6.3 | 7.5 | 6.8 | 8.2 |
| L-Alanine | 4.3 | 6.7 | 7.3 | 5.0 | 4.3 |
| L-Aspartic acid | 12.4 | 6.0 | 14.3 | 4.2 | 12.4 |
| L-Asparagine | 0 | 6.8 | 0 | 6.0 | 0 |
| L-Glutamic acid | 0 | 0 | 7.0 | 17.9 | 0 |
| L-Glutamine | 20.5 | 14.5 | 8.6 | 0.7 | 20.5 |
| Glycine | 4.3 | 3.9 | 4.1 | 2.8 | 4.3 |
| L-Proline | 5.8 | 3.9 | 5.1 | 7.6 | 5.8 |
| L-Serine | 5.3 | 7.0 | 9.4 | 4.2 | 5.3 |
| Amino acid (g/2000 ml) | 70 | 70 | 70 | 70 | 70 |
| Fat (g/2000 ml) | 0 | 0 | 0 | 0 | 22.2 |
| Carbohydrate (g/2000 ml) | 0 | 0 | 0 | 0 | 0 |

| Amino acid | Example No. | | Comparative Ex. No. | | | |
|---|---|---|---|---|---|---|
| (g/100 g) | 23 | 24 | 1 | 2 | 3 | 4 |
| L-Isoleucine | 5.2 | 5.2 | 7.4 | 7.4 | 7.4 | 7.4 |
| L-Leucine | 8.4 | 8.4 | 16.6 | 16.6 | 16.6 | 16.6 |
| L-Lysine | 6.5 | 6.5 | 20.1 | 20.1 | 20.1 | 20.1 |
| L-Phenylalanine | 5.7 | 5.7 | 11.7 | 11.7 | 11.7 | 11.7 |
| L-Threonine | 3.8 | 3.8 | 7.3 | 7.3 | 7.3 | 7.3 |
| L-Tryptophan | 1.4 | 1.4 | 2.4 | 2.4 | 2.4 | 2.4 |
| L-Tyrosine | 0 | 0 | 0 | 0 | 0 | 0 |
| L-Valine | 5.2 | 5.2 | 8.2 | 8.2 | 6.2 | 8.2 |
| L-Histidine | 2.9 | 2.9 | 4.0 | 4.0 | 4.0 | 4.0 |
| L-Arginine | 8.2 | 8.2 | 8.9 | 8.9 | 8.9 | 8.9 |
| L-Alanine | 4.3 | 4.3 | 0 | 0 | 0 | 0 |
| L-Aspartic acid | 12.4 | 12.4 | 0 | 0 | 0 | 0 |
| L-Asparagine | 0 | 0 | 0 | 0 | 0 | 0 |
| L-Glutamic acid | 0 | 0 | 0 | 0 | 0 | 0 |
| L-Glutamine | 20.5 | 20.5 | 0 | 0 | 0 | 0 |
| Glycine | 4.3 | 4.3 | 13.5 | 13.5 | 13.5 | 13.5 |
| L-Proline | 5.8 | 5.8 | 0 | 0 | 0 | 0 |
| L-Serine | 5.3 | 5.3 | 0 | 0 | 0 | 0 |
| Amino acid (g/2000 ml) | 70 | 70 | 70 | 70 | 70 | 70 |
| Fat (g/2000 ml) | 0 | 22.2 | 0 | 22.2 | 0 | 22.2 |
| Carbohydrate (g/2000 ml) | 380 | 380 | 0 | 0 | 380 | 380 |

Test Example 1

Yoshida sarcoma, $10^6$ cells/rat, was subcutaneously implanted at the back of male Donryu rats (7 weeks old). Two days after implantation, the rats were fasted overnight. On day 3 after implantation, an operation was performed to insert an indwelling catheter in the duodenum and the enteral feeding composition of Example 1 was administered intraduodenally (the invention group, n=8).

The volume of the above enteral infusion was 270 ml/kg. The dosing concentration, with 1 kcal/ml being regarded as 100% concentration, was 50% on the first day, 75% on the second day and 100% on the 3rd to 7th days. The rats were reared under the above test conditions for 7 days. Then, the rats were autopsied and the mean tumor weight of the test rats (n=8, mean g) was determined.

As a control, there was provided a group given a commercial elemental diet (Elental, Morishita Pharmaceutical) which was similarly administered in lieu of the anticancer enteral feeding composition of the invention (the control group, n=8).

The results are shown in FIG. 1, where tumor weights (g) are plotted on the ordinate and the mean value of each group is indicated as a bar.

It is apparent from FIG. 1 that the anticancer enteral feeding composition of the instant invention, administered enterally eternally, significantly reduces tumor weights in rats with Yoshida sarcoma (65% of control), indicating that the composition of the invention has tumor growth inhibitory activity.

Test Example 2

In the same manner as Test Example 1, 300 ml/kg of the anticancer enteral feeding composition of Example 1 was administered to rats according to the same dosing schedule as in Test Example 1. While the animals were similarly reared for 7 days, 5-FU was administered intraperitoneally to each rat (once daily, 10 mg/kg) on days 1, 2, 3, 4, 5 and 6 (the invention group, n=8).

After the above rearing period, the rats were autopsied and the mean tumor weight of the test rats was determined.

As a control, there was provided a group receiving a commercial elemental diet (Elental, Morishita Pharmaceutical) in lieu of the anticancer enteral feeding composition of the invention in the same manner (the control group, n=8). In addition, a free ingestion group receiving a commercial solid food (CRF-1, Oriental Yeast) (the 5-FU-free group, n=8; briefly referred to as the FF group) and another free ingestion group (5-FU group, n=8; briefly referred to as the 5 FU group) were also provided.

Figure 2:
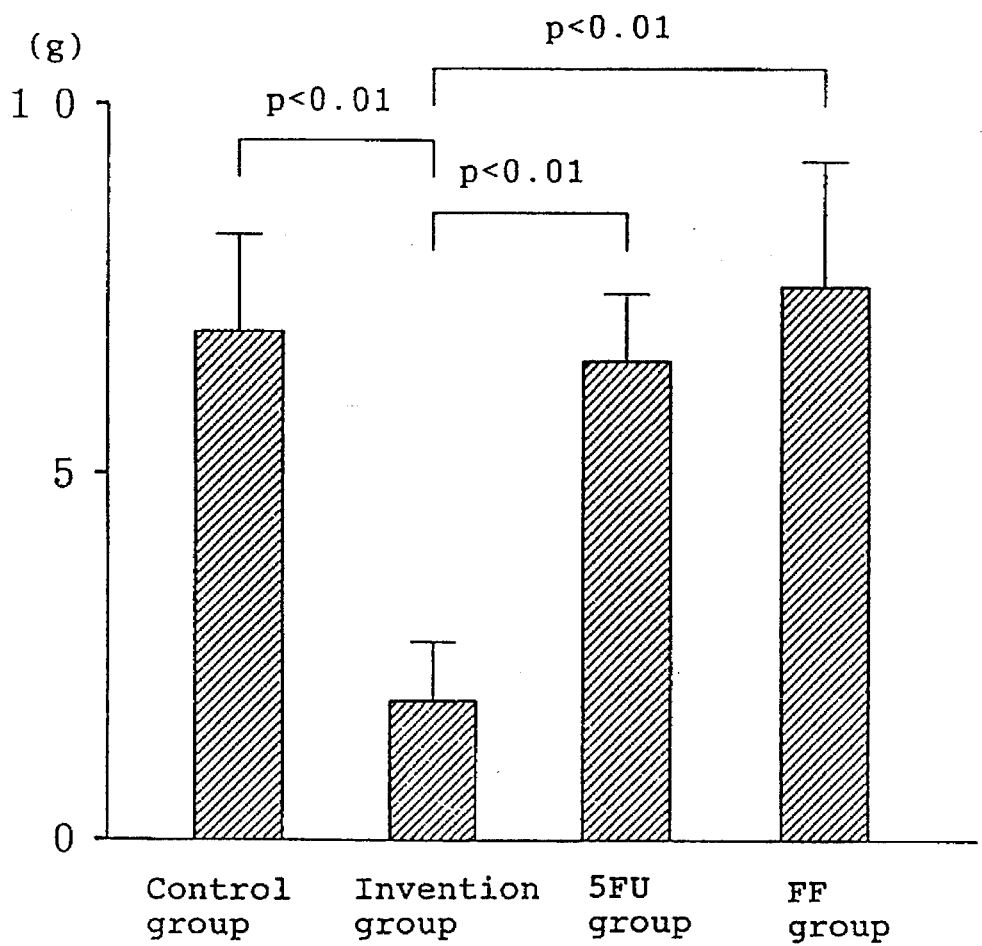
FIG. 2 is a diagrammatic representation of the tumor growth inhibitory effect of the combined use of the composition of the invention and an anticancer drug in Test Example 2.

The results are shown in FIG. 2, where tumor weights (g) are plotted on the ordinate and the mean value of each group is shown as a bar.

It is apparent from FIG. 2 that the anticancer enteral feeding composition of the invention administered in combination with an anticancer drug significantly reduces tumor weights in rats with Yoshida sarcoma and that, therefore, the enteral feeding composition of the invention synergistically potentiates the tumor growth inhibitory action of the anticancer drug.

Test Example 3

The procedure of Test Example 2 was repeated using the anticancer enteral feeding compositions obtained in Examples 1, 2 and 4 and, as a control, a commercial elemental diet (Elental). The group given the composition of Example 1 was designated as Example 1 group (n=8), the group given the composition of Example 2 as Example 2 group (n=7), the group given the composition of Example 4 as Example 4 group (n=6), and the group given the commercial elemental diet as Control group.

Figure 3:
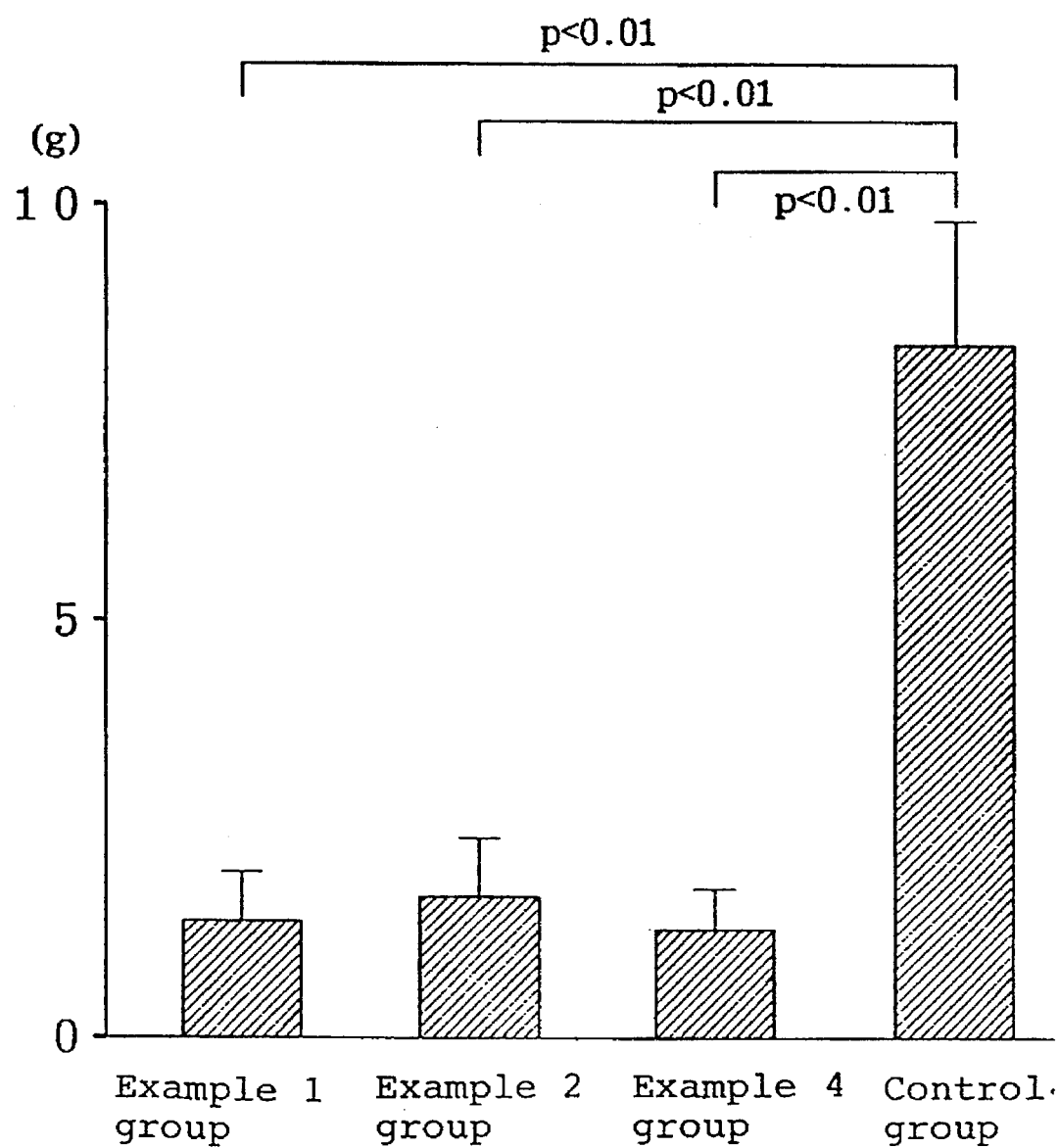
FIG. 3 is a diagrammatic representation of the tumor growth inhibitory effect of the combined use of the composition of the invention and an anticancer drug.

The results are shown in FIG. 3, which is similar to FIG. 2 in the manner of representation.

It is apparent from FIG. 3 that all the anticancer enteral feeding compositions of the invention have significant tumor growth inhibitory activity as compared with the commercial elemental diet.

Test Example 4

The anticancer enteral feeding composition of Example 1 was administered to tumor-bearing rats in the same manner as in Test Example 1. On days 1, 3, 5 and 7 after initiation of administration, the test animals were autopsied and the methionine level in the tumor mass was determined (the invention group).

As a control, there was provided a group of rats allowed free access to said commercial solid food (FF group).

Figure 4:
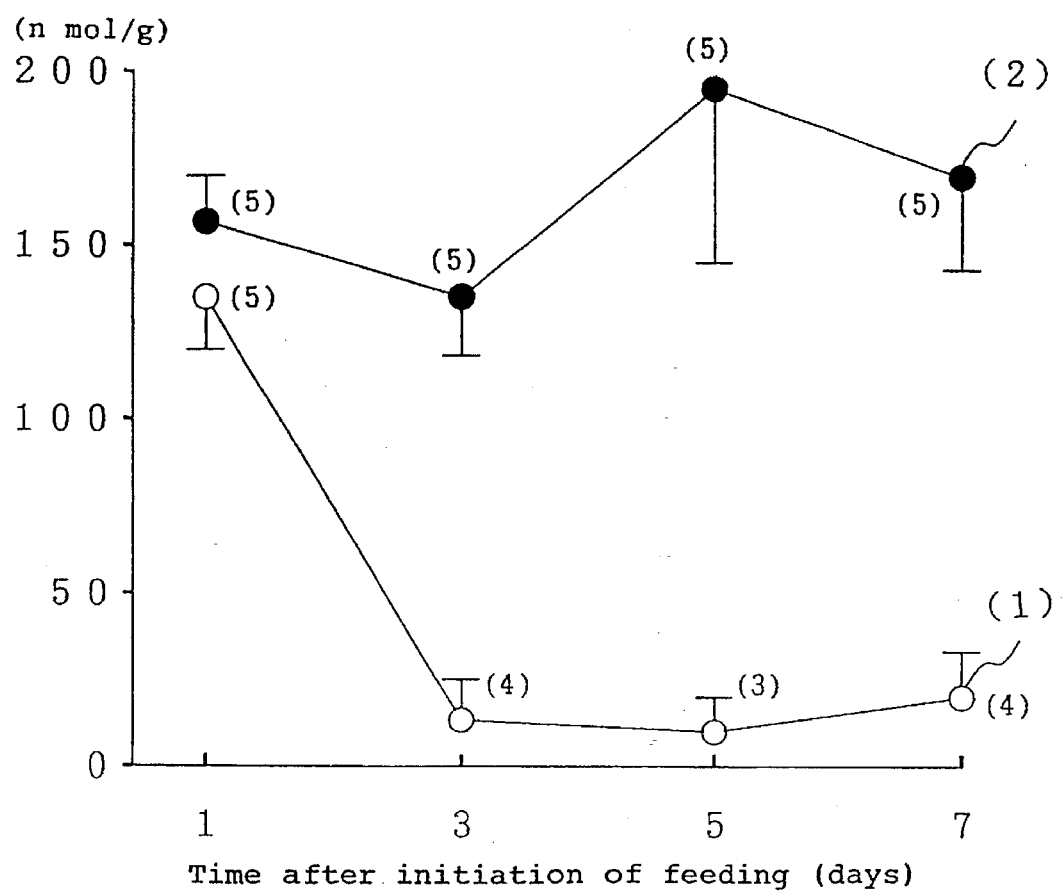
FIG. 4 is a diagrammatic representation of introtumoral methionine level in a tumor-bearing animal treated with the composition of the invention in Test Example 4.

The results are shown in FIG. 4. Here, the intratumoral methionine concentrations (n mol/g) were plotted on the ordinate, while the abscissa represents the number of days following the beginning of administration (days). In FIG. 4, (1) represents the invention group and (2) represents the FF group. The figure in parentheses denotes the number of animals autopsied (n) on the corresponding day.

It is apparent from FIG. 4 that the intratumoral methionine concentration on and after day 3 following the beginning of administration in the invention group remained very low and that was considered to be the reason why the composition of the invention exhibits strong tumor growth inhibitory activity as demonstrated in Test Example 1.

Test Example 5

Tumor growth inhibition assay of the powdery enteral feeding composition of the invention made available ad libitum in Yoshida sacroma-bearing rats Male Donryu rats (7 weeks old) were preliminarily reared with free access to a commercial elemental diet (Elental, Morishita Pharmaceutical). On day 5 after the beginning of preliminary feeding, Yoshida sarcoma, $10^6$ cells/rat, was subcutaneously implanted at the back of each rat. After an 8-day preliminary feeding, the powdery anticancer enteral feeding composition prepared in Example 1 was made available ad libitum for 7 days. Then, on days 1, 2, 3, 4, 5 and 6 after the beginning of main feeding, 5-FU was administered intaperitoneally to each rat (once daily, 10 mg/kg)(the invention group, n=7).

After completion of the above feeding, the rats were autopsied and the mean tumor weight (g) of the test rats was determined.

As a control, there was provided a group given a commercial elemental diet (Elental, Morishita Pharmaceutical) in lieu of the enteral feeding composition of the invention in a similar manner (the control group, n=7). There also was provided a group receiving said commercial elemental diet only and not given 5-FU (the commercial diet group, n=7).

Figure 5:
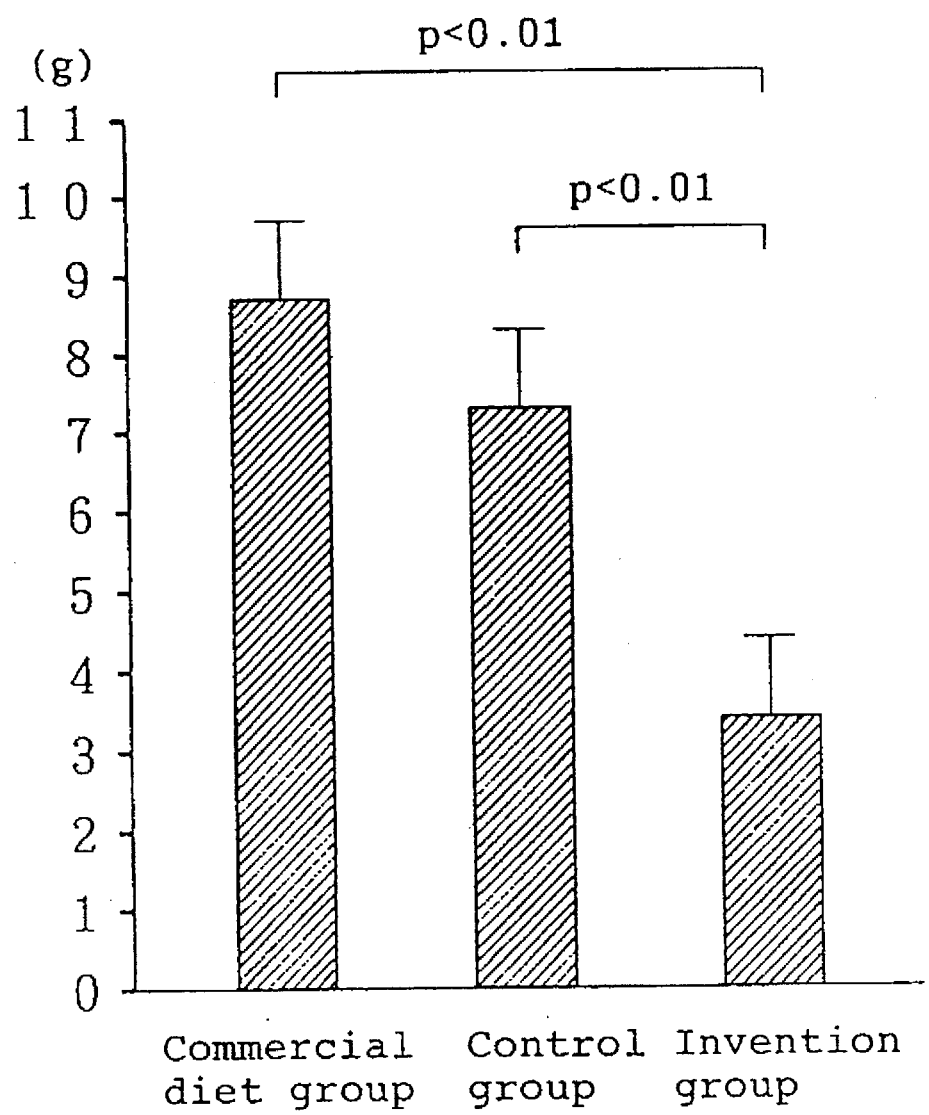
FIG. 5 is a diagrammatic representation of the tumor growth inhibitory effect of the combined use of the composition of the invention and an anticancer drug in Test Example 5.

The results are shown in FIG. 5. In the graph, tumor weights (g) are plotted on the ordinate and the mean value of each group is shown as a bar.

It is apparent from FIG. 5 that the combination of free ingestion of the anticancer enteral feeding composition of the invention with administration of an anticancer drug significantly reduces tumor weights in rats with Yoshida sarcoma and that, therefore, the anticancer enteral feeding composition of the invention synergistically potentiates the tumor growth inhibitory action of an anticancer drug not only in a continuous enteric administration modality but through oral administration (free ingestion).

Test Example 6

Tumor growth inhibition assay of the enteral preparation of the invention in an intermittent administration modality using rats with Yoshida sarcoma Yoshida sarcoma, $10^6$ cells/rat, was subcutaneously implanted at the back of male Donryu rats (7 weeks old). On day 2 after implantation, the animals were fasted overnight. On day 3 after implantation, an operation for inserting an indwelling catheter in the fore-stomach was performed and the anticancer enteric feeding composition prepared in Example 1 of the invention was administered intragastrically (the invention intermittent feeding group, n=7).

The dosage schedule for the above enteric feeding composition of the invention was 600 ml/kg in 2 hours×4 times (4 cycles of 2-hour administration and 4-hour withdrawal). The dosing concentration, with 1 kcal/ml being regarded as 100% concentration, was 50% on day 1, 75% on day 2 and 100% on days 3 to 7.

On days 1, 2, 3, 4, 5 and 6 after initiation of feeding, 5-FU was administered intraperitoneally to each rat (once daily, 10 mg/kg). The rats were reared under the above test conditions for 7 days, after which they were autopsied and the group mean tumor weight (g) was determined.

There also was provided a group given a 24-hour continuous administration of 200 ml/kg of the anticancer enteric feeding composition of the invention instead of intermittent administration and reared in the same manner for 7 days (the invention continuous feeding group, n=7).

Furthermore, there was provided a control group given a commercial solid food (CRF-1, Oriental Yeast) ad libitum instead of administration of the anticancer enteric feeding composition of the invention (the 5-FU group, n=7).

The results are shown in FIG. 6. In the graph, tumor weights (g) are plotted on the ordinate and the mean value of each group is indicated as a bar.

It is apparent from FIG. 6 that the combination of intermittent administration of the anticancer enteric feeding composition of the invention with administration of an anticancer drug significantly reduces tumor weights in rats with Yoshida sarcoma and that the anticancer enteric feeding composition of the invention synergistically potentiates the tumor growth inhibitory action of an anticancer drug not only in a continuous enteric administration modality but through intermittent administration or oral administration.

Test Example 7

An organoleptic evaluation test was performed using the aqueous amino acid solutions prepared in Examples 18–21, the amino acid-fat emulsion prepared in Example 22, the aqueous amino acid-carbohydrate solution prepared in Example 23, the amino acid-fat-carbohydrate emulsion prepared in Example 24 and the control aqueous solutions and emulsions prepared in Comparative Examples 1–4.

Thus, a panel of 10 healthy volunteers was instructed to evaluate the respective preparations in terms of odor, taste, and overall beverage quality on a 5-point scale ranging from 5 points for satisfactory (not objectionable at all) to 1 point (quite objectionable) and the mean score was calculated for each test preparation. The results are shown in Table 6. It should be understood that in regard to Examples 22–24 and the corresponding Comparable Examples 2–4, only the results of overall quality evaluation are presented in the table.

TABLE 6

| Test Preparation | Odor | Taste | Overall quality |
|---|---|---|---|
| Preparation of Ex. 18 | 4.0 ± 0.5** | 3.4 ± 0.5** | 3.4 ± 0.7** |
| Preparation of Ex. 19 | 3.9 ± 0.6** | 3.3 ± 0.5** | 3.3 ± 0.8** |
| Preparation of Ex. 20 | 3.8 ± 0.4** | 3.3 ± 0.5** | 3.4 ± 0.5** |
| Preparation of Ex. 21 | 3.9 ± 0.6** | 3.2 ± 0.4** | 3.4 ± 0.7** |
| Preparation of Comparative Ex. 1 | 1.3 ± 0.5 | 1.1 ± 0.3 | 1.1 ± 0.3 |

| Test preparation | Over all quality |
|---|---|
| Preparation of Ex. 22 | 3.4 ± 0.5** |
| Preparation of Comparative Ex. 2 | 1.2 ± 0.4 |
| Preparation of Ex. 23 | 3.7 ± 0.5** |

TABLE 6-continued

| | |
|---|---|
| Preparation of Comparative Ex. 3 | 1.4 ± 0.5 |
| Preparation of Ex. 24 | 3.9 ± 0.6** |
| Preparation of Comparative Ex. 4 | 1.4 ± 0.5 |

In the table, ** denotes a significant difference from the corresponding Comparative Example at P<0.01.

It will be apparent from the above table that all the compositions prepared in the examples of the invention are significantly superior to those prepared in the comparative examples in organoleptic evaluation and that they are enteric nutritive preparations quite satisfactory in taste and odor.

Test Example 8

Pharmaceutical stability test of the enteric feeding compositions of the invention The powdery anticancer enteric feeding compositions obtained in Example 1 and control powdery preparations a and b prepared in the following manners were compared in regard to appearance, solubility and state of emulsion.

Preparation of control powdery preparation a

In 5000 ml of purified water were dissolved 600 g of dextrin (Matsutani Chemical).

On the other hand, 10 g of soya lecithin (Epikuron 100, Nihon Sieber Hegner) were dissolved in 222 g of soybean oil (Nippon Oils and Fats) with heating, while 30 g of sucrose fatty acid ester (DK-F160, Daiichi Kogyo Seiyaku, HLB=15) were dissolved in 1000 ml of purified water similarly with heating. The three solutions were combined and spray-dried as in Example 1 to give 780 g (100%=862 g) of a powder.

To 430 g of the above powder were added 1500 g of granulated dextrin, an amino acid mixture (one-half of the composition of Example 1) and a homogeneous mixture of the same minerals and vitamins as used in Example 1 in 100 g of granulated dextrin and the whole mixture was homogenized to give a powdery nutritive composition (control powdery preparation a).

Preparation of control powdery preparation b

In 5000 ml of purified water were dissolved 3800 g of dextrin (Matsutani Chemical), an amino acid mixture of the same composition as that used in Example 1, and minerals and vitamins (twice the amounts used in Example 1) with heating.

On the other hand, 10 g of soya lecithin (Epikuron 100, Nihon Sieber Hegner) were dissolved in 222 g of soybean oil (Nippon Oils and Fats) with heating, while 30 g of sucrose fatty acid ester (DK-F160, Daiichi Kogyo Seiyaku, HLB=15) were dissolved in 1000 ml of purified water. The three solutions were combined and spray-dried as in Example 1 to give a powdery nutritive composition (control powdery preparation b).

The respective preparations were evaluated and tested for appearance, solubility and emulsion state. Thus, the appearance of each powder was visually inspected immediately after preparation. Then, 250 g of each powder was put in an enteral dosing bag (made of polyvinyl chloride) and, after 880 ml of water were added, shaken to mix for about 1 minute. The solubility was then evaluated by visual inspection. The state of emulsification of the liquid was also visually inspected and the diameter of emulsion particles was measured using a laser particle analyzer (Otsuka Electronics). In addition, the mixed fluid was allowed to stand at room temperature for 48 hours and the state of the fluid was then visually evaluated.

TABLE 7

| | Preparation of Example 1 | Control powdery preparation a | Control powdery preparation b |
|---|---|---|---|
| Appearance of powder | Light yellow | Light yellow | Yellow |
| Solubility | Rapidly dispersed and homogenized | Small insoluble masses afloat on the liquid surface | Flocculation occurred |
| State of emulsion | Homogeneous and stable | Abundant insoluble matter | Homogeneous and stable |
| Emulsion particle size | 190 nm | 450 nm | 200 nm |
| State of fluid after 48 hours | Homogeneous and stable | Small insoluble masses afloat on the liquid surface | Separated into two layers |

We claim:

1. A composition for enteric absorption which comprises a powder, obtainable by emulsifying a fat in an aqueous solution of protein source amino acids and spray-drying the resulting oil-in-water emulsion, and granulated dextrin, which composition forms a stable oil-in-water emulsion when mixed with water, wherein said protein source amino acids comprise, in free amino acid equivalent amounts,

| L-Amino Acid | (g/100 g) |
|---|---|
| Isoleucine | 2.58–10.30 |
| Leucine | 4.21–16.82 |
| Lysine | 3.26–13.06 |
| Phenylalanine | 2.84–8.51 |
| Threonine | 1.89–5.67 |
| Tryptophan | 0.72–2.15 |
| Valine | 2.58–10.30 |
| Histidine | 1.46–4.38 |
| Arginine | 4.12–16.48 |
| Alanine | 2.15–8.58 |
| Aspartic acid and/or asparagine | 6.18–24.72 |
| Glutamic acid and/or glutamine | 10.31–41.22 |
| Glycine | 2.15–8.58 |
| Proline | 2.92–11.68 |
| Serine | 2.66–10.64 |
| Tyrosine | 0–3.0. |

2. The composition of claim 1, wherein the protein source amino acids comprise, in free amino acid equivalent amounts,

| L-Amino Acid | (g/100 g) |
|---|---|
| Isoleucine | 2.58–7.73 |
| Leucine | 4.21–12.62 |
| Lysine | 3.26–9.80 |
| Phenylalanine | 2.84–8.51 |
| Threonine | 1.89–5.67 |
| Tryptophan | 0.72–2.15 |
| Valine | 2.58–7.73 |
| Histidine | 1.46–4.38 |
| Arginine | 4.12–12.36 |
| Alanine | 2.15–6.44 |
| Aspartic acid and/or asparagine | 6.18–18.54 |
| Glutamic acid and/or glutamine | 10.31–30.92 |

-continued

| L-Amino Acid | (g/100 g) |
|---|---|
| Glycine | 2.15–6.44 |
| Proline | 2.92–8.76 |
| Serine | 2.66–7.98 |
| Tyrosine | 0–2.0. |

3. The composition of claim 1, wherein the protein source amino acids comprise, in free amino acid equivalent amounts,

| L-Amino Acid | (g/100 g) |
|---|---|
| Isoleucine | 3.86–6.44 |
| Leucine | 6.31–10.51 |
| Lysine | 4.90–8.16 |
| Phenylalanine | 4.25–7.09 |
| Threonine | 2.84–4.73 |
| Tryptophan | 1.07–1.79 |
| Valine | 3.86–6.44 |
| Histidine | 2.19–3.65 |

-continued

| L-Amino Acid | (g/100 g) |
|---|---|
| Arginine | 6.18–10.30 |
| Alanine | 3.22–5.36 |
| Aspartic acid and/or asparagine | 9.27–15.45 |
| Glutamic acid and/or glutamine | 15.46–25.76 |
| Glycine | 3.22–5.36 |
| Proline | 4.38–7.30 |
| Serine | 3.99–6.65 |
| Tyrosine | 0–1.0. |

4. The composition of claim 1, which contains, in each 2000 kcal of the composition, 40–100 g of amino acids, 11.1–66.6 g of fat and 250–435 g of dextrin.

5. The composition of any of claims 4, or 3 wherein an emulsifier with an HLB number of 9 to 16 is used in an amount within the range of 2.5–10 weight % based on the total weight of said fat and amino acids.

* * * * *